(12) United States Patent
Saito et al.

(10) Patent No.: US 6,635,488 B1
(45) Date of Patent: Oct. 21, 2003

(54) AUTOMATED ANALYZER AND AUTOMATED ANALYSIS

(75) Inventors: Michihiro Saito, Kashiwa (JP); Koshin Tagami, Nakamachi (JP)

(73) Assignee: Hitachi, Ltd., Tokyo (JP)

( * ) Notice: Subject to any disclaimer, the term of this patent is extended or adjusted under 35 U.S.C. 154(b) by 308 days.

(21) Appl. No.: 09/598,048

(22) Filed: Jun. 21, 2000

(30) Foreign Application Priority Data

Jun. 22, 1999 (JP) .......................................... 11-175637

(51) Int. Cl.$^7$ ................................................ G01N 35/02
(52) U.S. Cl. ..................... 436/43; 436/47; 436/49; 436/165; 422/63; 422/67
(58) Field of Search .................. 436/43–49, 54, 436/165, 172; 422/63, 64, 67

(56) References Cited

U.S. PATENT DOCUMENTS 5,482,861 A * 1/1996 Clark et al. ................... 422/63

FOREIGN PATENT DOCUMENTS

| JP | 63-200066 | 8/1988 |
|---|---|---|
| JP | 2-87069 | 3/1990 |

* cited by examiner

Primary Examiner—Lyle A. Alexander
(74) Attorney, Agent, or Firm—Mattingly, Stanger & Malur, P.C.

(57) ABSTRACT

An automated analyzer which analyzes a sample which might have been affected by carryover, judges the effect of carryover from the analytical value, and indicates the result. The automated analyzer also performs analysis on a specific inspection item necessary for a sample which might have been affected by carryover from its preceding sample and modifies the result of analysis of said sample according to the analytical value.

5 Claims, 6 Drawing Sheets

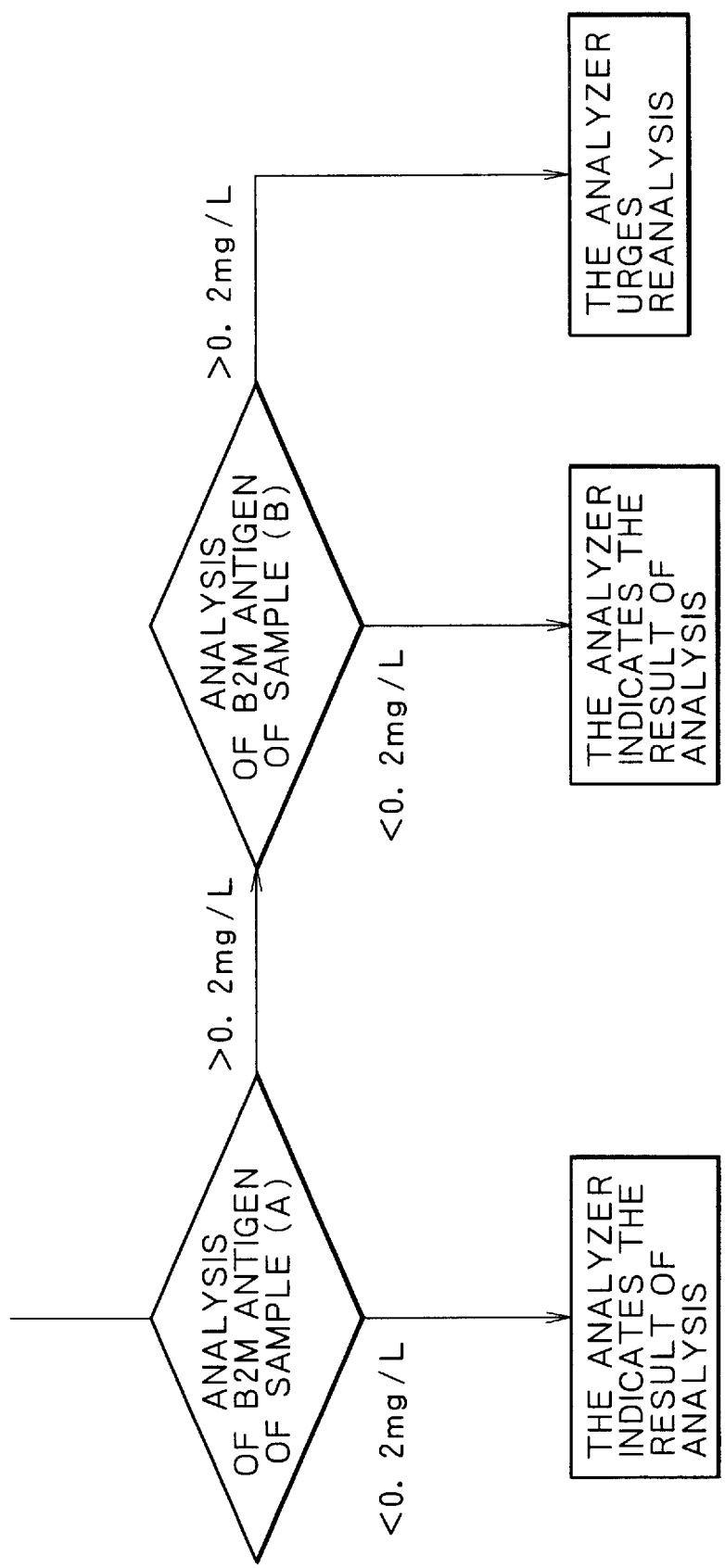

AUTOMATED ANALYZER AND AUTOMATED ANALYSIS

BACKGROUND OF THE INVENTION

The present invention relates to an automated analyzer and automated analysis, and more particularly, to an automated analyzer and automated analysis applicable to those samples which are certainly or uncertainly subject to carryover.

Carryover from one sample to another sometimes takes place in any automated analyzer. It gives incorrect analytical data. For example, an intrinsically negative or normal sample would be regarded as positive or abnormal or a normally low value is rated as high, as the result of carryover. The fluctuation of data due to carryover nullify the results of analysis. It is empirically known that carryover from one sample to another takes place when samples are handled by the sample dispenser, the reagent suction dispenser, the cleaning pipetter, and the like.

It is possible to predict in what inspection item carryover takes place or carryover affects test results if actual analysis are performed on several samples for several inspection items combined together during development of new apparatus.

One way to prevent the fluctuation of analytical data due to carryover has been to thoroughly wash the piptters for samples which are known or supposed to be subject to carryover. Unfortunately, washing needs a large amount of cleaning solution and decreases the sample handling capacity of the apparatus per unit time. Moreover, there is even an instance where it is technically impossible to avoid carryover in such a way.

It is possible to run (or program) an automated analyzer in such a way that analyses for the same sample are performed first on the inspection item which is most vulnerable to the effect of carryover and then on the inspection item which is less (or least) vulnerable to the effect of carryover. That is, when the inspection item which is most vulnerable to the effect of carryover and the inspection item which is less (or least) vulnerable to the effect of carryover are analyzed in the same automated analyzer, the former is analyzed first and the latter is analyzed subsequently so that the analysis is performed in an effective way.

For example, Japanese Patent Laid-open No. Hei 2-87069 discloses a method of avoiding the effect of intercontamination of reagents without decrease in processing speed and loss of reagents by proving means to change part or all of the designated sequence of analysis. Also, Japanese Patent Laid-open No. Sho 63-200066 discloses an analytical instrument which is so designed as to prevent reagents from interfering with one another by altering and controlling the order of measurements for the items of analysis according to stored information about reagents.

However, this method has the disadvantage that an analysis of inspection item vulnerable to the effect of carryover has to be omitted or performed on a newly taken sample if it is to follow an analysis of inspection item not vulnerable to the effect of carryover or an analysis of other inspection items.

There may be an instance where a sample which has been analyzed once or more is analyzed again for the inspection item vulnerable to the effect of carryover according to a doctor's instruction. In addition, the instrument would fail, for some reason or other, in the analysis for a certain inspection item which is to be performed first. Moreover, there is a possibility that analysis for some inspection item has to be repeated. In this case, it is necessary to take a new sample, giving pain to patients.

According to the prior art, it is common practice to lessen carryover technically and, if this is not practical, then skip analysis for the inspection item vulnerable to the effect of carryover. No attempts have been made to let the automated analyzer judge by itself whether actual measurements are reliable with the effect of carryover taken into account. There has been no automated analyzer capable of indicating the results of measurements based on the data of samples causing carryover as well as samples suffering carryover.

SUMMARY OF THE INVENTION

It is an object of the present invention to provide an automated analyzer which performs analysis on a sample which might have suffered carryover during its single or repeated automated analyses and then indicates the results, with the effect of carryover taken into account. The automated analyzer, therefore, contributes to efficient operation.

It is another object of the present invention to provide an automated analyzer which, in handling an inspection item which might have been affected by carryover, performs analyses on a sample which might have caused carryover for its necessary inspection items, and then indicates the results, with the effect of carryover taken into account. The automated analyzer, therefore, contributes to efficient operation.

The automated analyzer according to one aspect of the present invention performs automated analyses for an inspection item which might have been affected by carryover in the past one or more analyses and indicates the results of analyses (negative or positive, or normal or abnormal) after taking into account the effect of carryover.

The automated analyzer according to another aspect of the present invention performs automated analyses in such a way that, if it regards a sample as abnormal, it performs analysis again on another sample which might have caused carryover to that sample and then it indicates the results of analyses (negative or positive, or normal or abnormal) after taking into account the effect of carryover.

The automated analyzer according to still another aspect of the present invention performs automated analysis on a single sample once or more times while performing automated analysis (simultaneously with, before or after said analysis) on another sample which might have caused carryover to the preceding sample.

BRIEF DESCRIPTION OF THE DRAWINGS

FIG. 6 is a flow chart showing the sequence of a program for re-analysis (in FIG. 4) practiced in Example 2.

DESCRIPTION OF THE PREFERRED EMBODIMENTS

In what follows, the present invention will be described in more detail with reference to the accompanying drawings.

Figure 1:
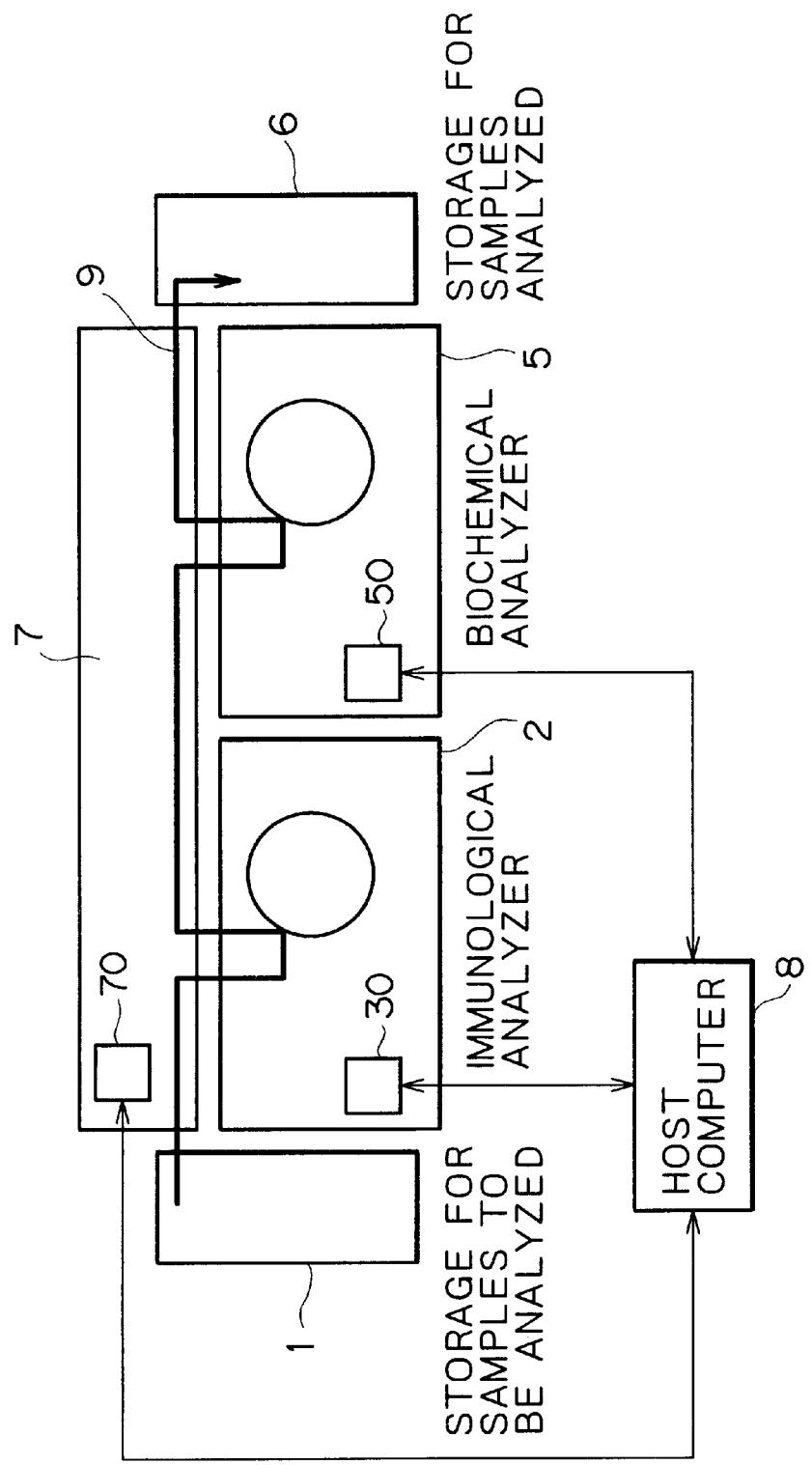
FIG. 1 is a schematic diagram showing an integrated system of biochemical analyzer and immunological analyzer to which the present invention is applied.
Figure 2:
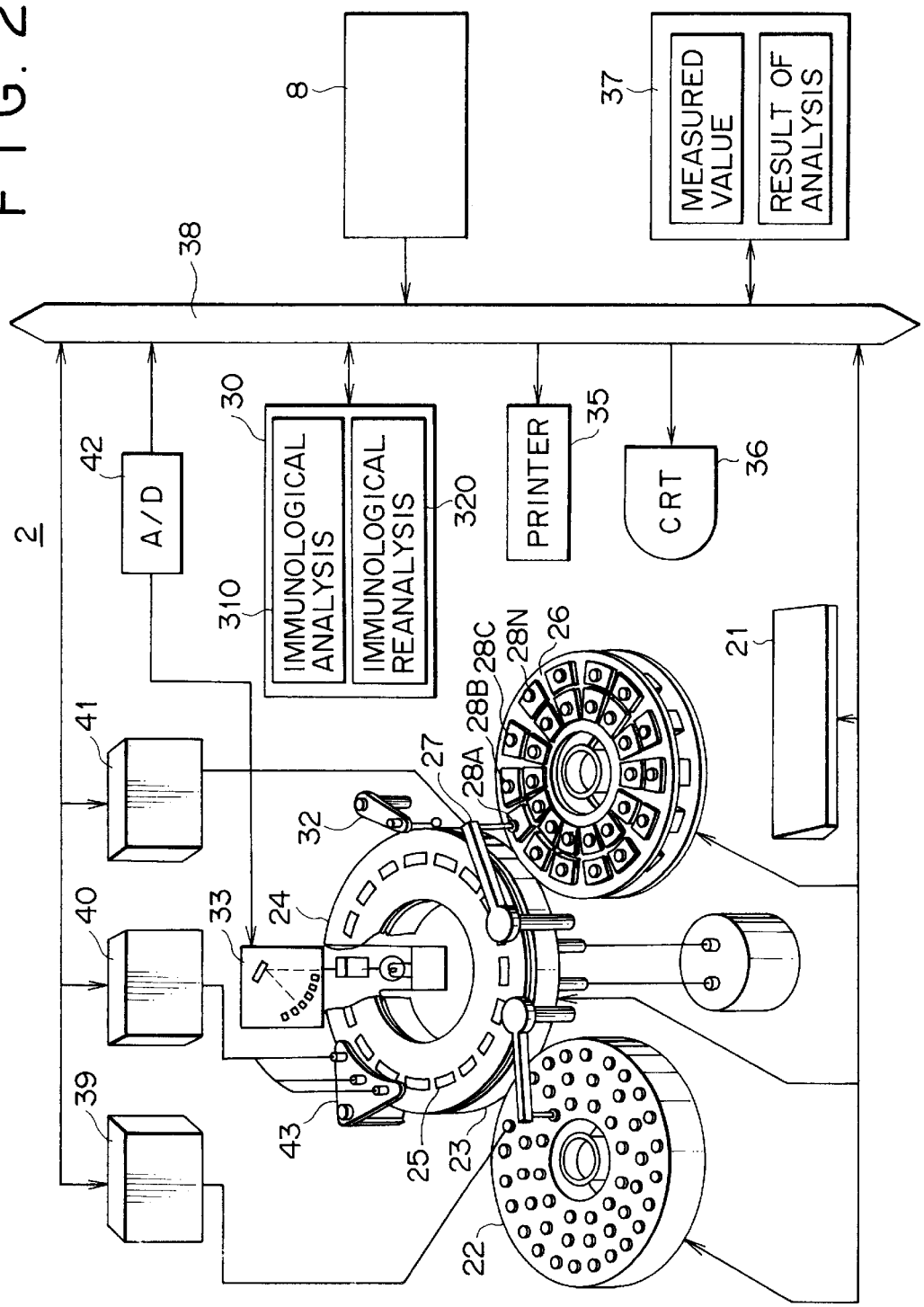
FIG. 2 is a diagram showing the detail of the immunological analyzer shown in FIG. 1.

FIG. 1 shows an integrated system of biochemical analyzer and immunological analyzer to which the present invention is applied. FIG. 2 shows the detailed structure of the immunological analyzer.

Reference numerals in FIG. 1 denote the components as follows:
- a storage 1 for samples to be analyzed;
- an automated analyzer 2 (such as immunological analyzer) arranged upstream so as to avoid carryover;
- an automated analyzer 5 (such as biochemical analyzer) which is liable to cause carryover;
- a storage 6 for samples analyzed;
- an ordinary sample carrying line 7;
- a host computer 8 consisting of:
  - a microcomputer 30 as a control unit to control the immunological analyzer 2;
  - a microcomputer 50 as a control unit to control the biochemical analyzer; and
  - a microcomputer 70 as a control unit to control the sample carrier line 7.

As shown in FIG. 2, each automated analyzer has a control panel 21, a sample disk 22, a sampling probe 23, a reaction disk 24, a reagent disk 26, a stirrer 32, a printer 35, a display 36, an external storage 37, an interface 38, a sample dispenser 39, a cleaning water supplier 40, a reagent dispenser 41, an A/D converter 42, and a washing mechanism 43.

The microcomputer 30 controls the immunological analyzer 2 as an automated analyzer in response to the flow 9 of samples being carried to analyzers through the sample carrying line 7. For this purpose it has a program 310 for immunological analysis which specifies the procedure and calculation of ordinary automated analysis. It also has another program 320 for reanalysis to be performed on a sample which might have suffered carryover in the preceding one or more analyses. This program judges whether the measured values are affected by carryover and indicates the results (normal or abnormal) on the display 36. These programs 310 and 320 may be combined into one. For brevity, the following description is limited to the program 320 to repeat immunological analysis.

The immunological analyzer 2 works as follows according to the program mentioned above. First, the control panel 21 receives a request for analysis. In response to this request, the sampling probe 23 sucks up the sample placed on the sample disk 22 and then it discharges the sample into the reaction vessel 25 on the reaction disk 24. Sampling is performed repeatedly on the same sample according to the request. The quantity to be taken varies depending on the inspection items. Then, the reagent pipetting mechanism 27 sucks up the reagents 28 (28A to 28N) placed on the reagent disk 26 and discharges them into the reaction vessel 25, so that reactions start. After a prescribed period of time, the photometer 33 examines the solution and the microcomputer 30 performs calculations and displays the results. These steps are repeated sequentially. The measured values and the results of analyses are recorded and stored in the microcomputer 30, host computer 8, or external memory 37.

Figure 3:
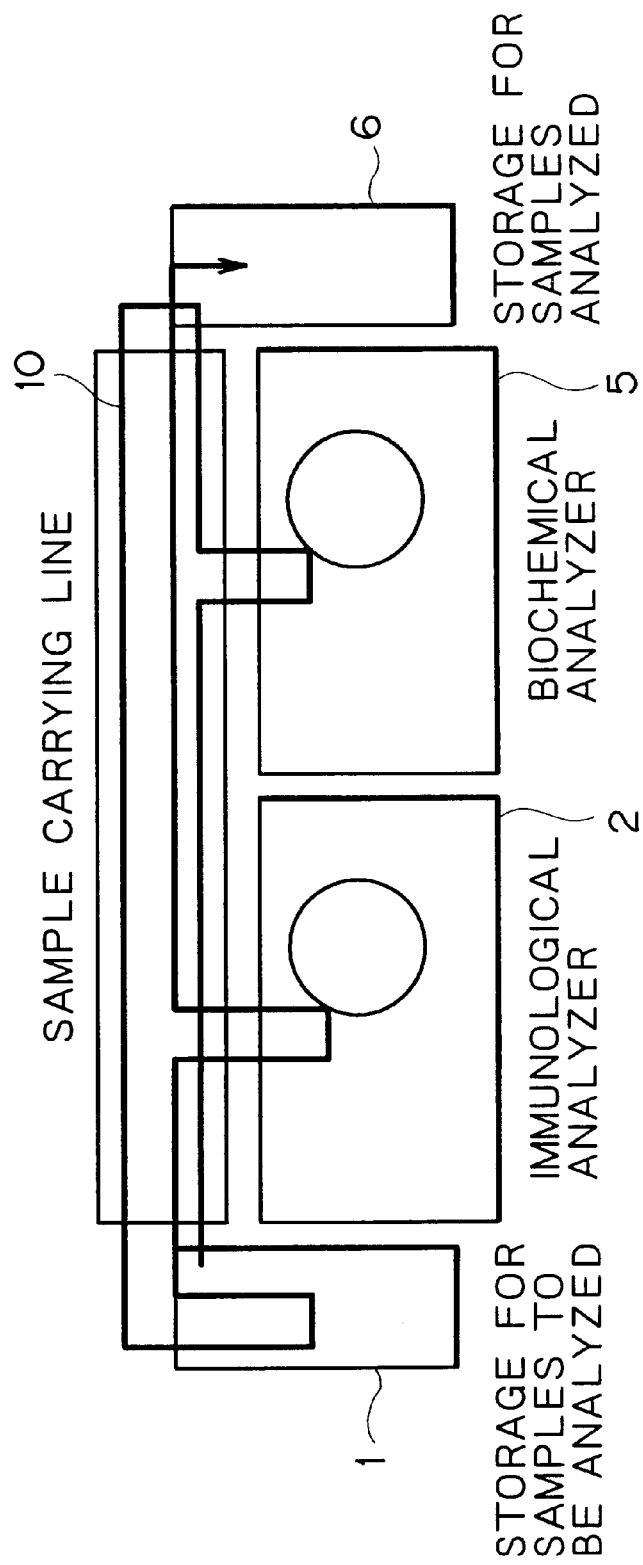
FIG. 3 is a schematic diagram showing a sample carrier line to which the present invention is applied.

The reanalysis of samples as shown by a sample carrying line in FIG. 3 is intended to perform analysis again (using the immunological analyzer) on those samples which have been analyzed by the immunological analyzer 2 or the biochemical analyzer 5 (which is likely to cause carryover). In other words, it is intended for those samples which have been analyzed once or more and for those inspection items which might have been affected by carryover. Reanalysis may also be necessary when the automated analyzer ends in failure or when a doctor wants to reconfirm the results obtained previously. When a new request is made for those inspection items which have not yet been examined, reanalysis may be performed on those samples which have been analyzed once or more already.

Figure 4:
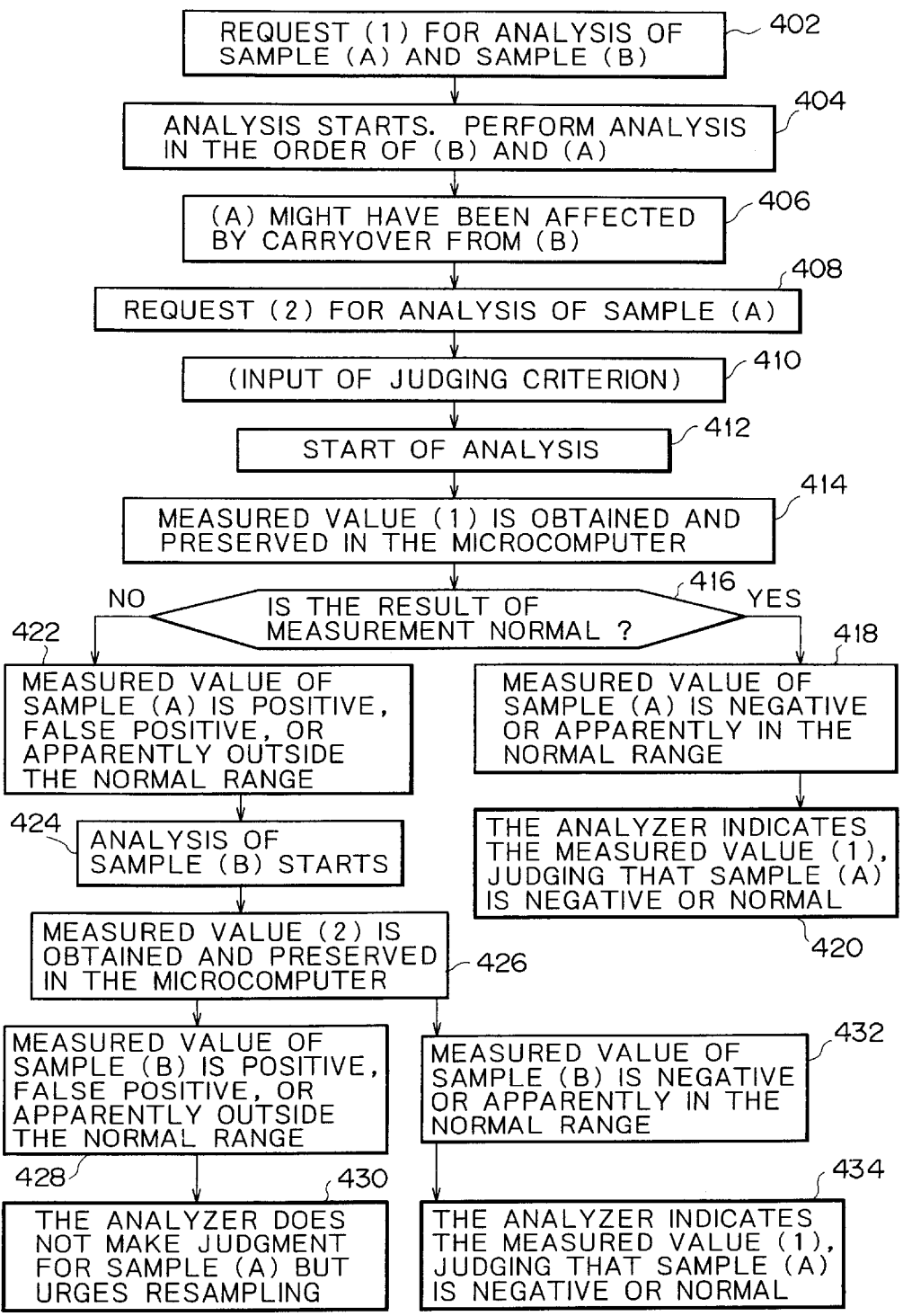
FIG. 4 is a flow chart showing the sequence of a program for reanalysis as one embodiment of the present invention.

One embodiment of the present invention is explained below with reference to the flow chart in FIG. 4 which shows the procedure of processing by the reanalysis program 320 of the microcomputer 30.

It is assumed that a first request (1) is made for analysis of sample (A) and sample (B) and then a second request is made for reanalysis of sample (A).

In step 402, a first request (1) for analysis of sample (A) and sample (B) is received. In step 404, analysis is performed sequentially on sample (B) and sample (A). Incidentally, the request (1) is processed in the ordinary way adopted for automated analysis.

The results of analysis suggest the possibility of sample (A) having suffered carryover from sample (B). This is recorded in the external storage 37 (in step 406). It is assumed that a second request (2) is made for reanalysis of sample (A) (in step 408). In response to this request, the operator enters into the control panel 21 the criterion of judgment for the inspection item requested (in step 410). Analysis starts (in step 412). The measured value (1) is obtained. The measured value and the criterion for judgment are preserved in the storage of the microcomputer (in step 414).

Then, judgement is made on whether the measured value (1) is normal or not according to the aforesaid criterion (in step 416). If the measured value of the sample (A) is negative or apparently normal (in step 418), the sample (A) is judged as negative or normal, and the measured value (1) is indicated on the display 36 (in step 420).

If the measured value of the sample (A) is positive, or false positive or nearly normal (in step 422), then the analysis of the sample (B) is started (in step 424). Thus the measured value (2) is produced, and it is preserved, together with the judging criterion, in the microcomputer's storage (in step 426). Then, judgment is made whether the measured value (2) is normal or not according to the aforesaid judging criterion. If the measured value of sample (B) is normal (or negative) or is apparently in the normal range (in step 432), then sample (A) is judged to be negative or normal and the measured value (1) is indicated on the display 36 (in step 434). On the other hand, if the measured value of sample (B) is abnormal (or positive) or apparently outside the normal range (in step 428), then no judgment is made for sample (A) but a message is shown on the display 36 so that it is necessary to take another sample from the patient (in step 430).

The following are concrete examples demonstrating the judgment with the effect of carryover taken into account.

EXAMPLE 1

This example is explained with reference to FIG. 5. It is assumed that an integrated system of biochemical analyzer and immunological analyzer is utilized to analyze GPT (as an item of biochemical analysis for diagnosis of liver function) and then detect hepatitis virus (as an item of immunological analysis) by the test for HBs antigen. It is expected that the serum sample (A) is contaminated with a carryover (1–2000 ppm) from the serum sample (B) which has undergone GPT analysis.

Figure 5:
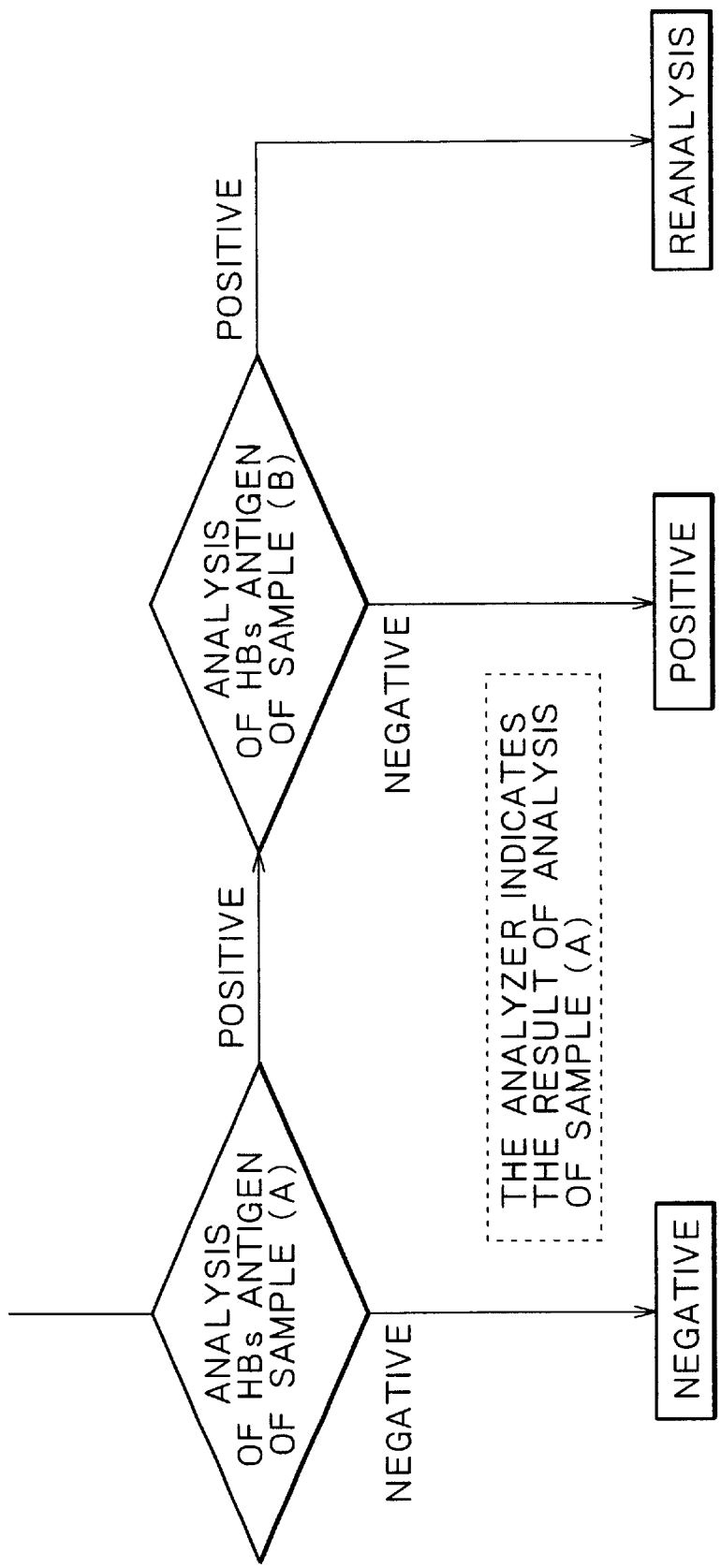
FIG. 5 is a flow chart showing the sequence of a program for reanalysis (in FIG. 4) practiced in Example 1.

According to the present invention, the automated analyzer is programmed such that it carries out tests following the flow chart shown in FIG. 5 and indicates or prints the result (in the format shown in Table 1) on the display 36 or the printer 35, respectively.

(1) The measured value of sample (A) has been found negative for HBs antigen.
Then, the analyzer indicates that the result of analysis of sample (A) is negative.
(2) The measured value of sample (A) has been found positive for HBs antigen, and the measured value of sample (B) has been found negative for HBs antigen.
Then, the analyzer indicates that the result of analysis of sample (A) is positive.
(3) The measured value of sample (A) has been found positive for HBs antigen and the measured value of sample (B) has been found positive for HBs antigen.
Then, the analyzer masks the result of analysis of sample (A) and indicates that it is necessary to take a sample again and to perform analysis again.

TABLE 1

| Analysis of sample (A) for HBs antigen | Analysis of sample (B) for HBs antigen | Analysis of sample (A) for HBs antigen | Analysis of sample (A) for HBs antigen |
|---|---|---|---|
| Measured value (1) | Measured value (2) | Result indicated | Measured value indicated |
| Negative | Negative | Negative | Value of (1) |
| Negative | Positive | Negative | Value of (1)* |
| Positive | Negative | Positive | Value of (1) |
| Positive | Positive | Reanalysis | None |

Value of (1): The analyzer gives the result as measured value (1). The analyzer may also indicate the calculated value of {value of (1)–value of (2)}÷1000.
Value of (1)*: The analyzer indicates the value obtained by measured value (1) or indicates the calculated value of {value of (1)–value of (2)}÷1000.
This formula of calculation varies depending on the amount of carryover and the item of inspection. It is assumed in this case that the amount of carryover is 1000 ppm (1/1000).

In analysis of HBs antigen, the analyzer may be set up such that the analyzer analyzes sample (B) after the analyzer has obtained the result of analysis of sample (A) or the analyzer analyzes samples (A) and (B) consecutively before it obtains the result of analysis of sample (A).

The analyzer may also indicate the measured value of sample (A) for the purpose of reference. In this case, the indicated value is the value which is calculated by subtracting the value (which is higher than normal due to anticipated carryover) from the measured value of sample (A).

If sample (B) is found positive, the analyzer may divide the measured value into two or more classes-weak positive and strong positive, and so on, so that the result of analysis of sample (A) is interpreted meaningfully. (See Table 2.)

TABLE 2

| Analysis of sample (A) for HBs antigen | Analysis of sample (B) for HBs antigen | Analysis of sample (A) for HBs antigen | Analysis of sample (A) for HBs antigen |
|---|---|---|---|
| Measured value (1) | Measured value (2) | Result indicated | Measured value indicated |
| Negative | Negative | Negative | Value of (1) * |
| Negative | Positive | Negative | Value of (1) * |
| Positive | Negative | Positive | Value of (1) |
| Positive | Weak positive *1 | Positive | {value of (1) – value of (2) } ÷ 1000 |
| Positive | Strong positive *2 | Reanalysis | None |

{value of (1)–value of (2)}÷1000: The analyzer indicates the calculated value of {value of (1)–value of (2)}÷1000, or indicates the measured value (1). In this case, 1000 ppm of carryover is assumed.

In the same way as above, if sample (B) is found positive, the analyzer may divide the measured value into several classes so that the result of analysis of sample (A) is interpreted meaningfully. The analyzer may also divide the measured value of sample (A) and indicates the value of sample (A) which is calculated by taking into account an increase due to anticipated carryover from sample (B).

EXAMPLE 2

This example (for the criterion of judgment) is explained with reference to FIG. 6. It is assumed that an automated biochemical analyzer is utilized to analyze GPT (as an item of biochemical analysis for diagnosis of liver function), and then an immunological analyzer analyzes β-2-microglobulin (B2M) (as an item of immunological analysis for kidney function). It is expected that the serum sample (A) is contaminated with a carryover (1000 ppm) from the serum sample (B) which has undergone GPT analysis. A normal range of the B2M value is approximately 0.2 mg/l or less.

According to the present invention, the automated analyzer is programmed such that it carries out tests following the flow chart shown in FIG. 6 and indicates or prints the result (in the format shown in Table 3) on the display 36 or the printer 35, respectively.

(1) The measured value of sample (A) has been found to be 0.1 mg/l which is normal for B2M.
Then, the analyzer indicates that the result of analysis of sample (A) is 0.1 mg/l.
(2) The measured value of sample (A) has been found to be 1.0 mg/l which is outside the normal range for B2M; and the measured value of sample (B) has been found to be 0.1 mg/l which is normal for B2M.
Then, the analyzer indicates that the result of analysis of sample (A) is 1.0 mg/l.
(3) The measured value of sample (A) has been found to be 1.1 mg/l which is normal for B2M; and the measured value of sample (B) has been found to be 10 mg/l which is outside the normal range.
Then, the analyzer masks the result of analysis of sample (A) and indicates that it is necessary to take a sample again and to perform analysis again. Alternatively, the analyzer indicates the value of 1 mg/l or the value of 1.1 mg/l, the former being calculated by subtracting the value of anticipated carryover from the result of analysis of sample (A), and the latter being calculated by not subtracting the value of anticipated carryover from the result of analysis of sample (A). In other words, the analyzer tells with considerably high probability that the result is outside the normal range.

TABLE 3

| Analysis of sample (A) for B2M | Analysis of sample (B) for B2M | Analysis of sample (A) for B2M | Analysis of sample (A) for B2M |
|---|---|---|---|
| Measured value (1) | Measured value (2) | Result indicated | Comments indicated |
| <0.2 mg/l (normal value) | <0.2 mg/l (normal value) | Value of (1) * | (Normal) |
| <0.2 mg/l (normal value) | 0.2 mg/l < (abnormal value) | Value of (1) * | (Normal) |
| 0.2 mg/l < (abnormal value) | <0.2 mg/l (normal value) | Value of (1) * | (Abnormal) |
| 0.2 mg/l < (abnormal value) | 0.2 mg/l < (abnormal value) | Reanalysis | none |

Value of (1): The analyzer gives the result as measured value (1). The analyzer may also indicate the calculated value of {value of (1)–value of (2)}÷1000.

This formula of calculation varies depending on the amount of carryover and the item of inspection. It is assumed in this case that the amount of carryover is 1000 ppm (1/1000).

In analysis of B2M antigen, the analyzer may be set up such that it analyzes sample (B) after it has known the result of analysis of sample (A) or it analyzes samples (A) and (B) consecutively before it knows the result of analysis of sample (A).

If the measured value of sample (B) is in the abnormal range, the analyzer may divide the measured value into two or more classes-weak positive and strong positive, and so on, so that the result of analysis of sample (A) is interpreted meaningfully. (See Table 4.)

TABLE 4

| Analysis of sample (A) for B2M | Analysis of sample (B) for B2M | Analysis of sample (A) for B2M | Analysis of sample (A) for B2M |
| --- | --- | --- | --- |
| Measured value (1) | Measured value (2) | Result indicated | Comments indicated |
| <0.2 mg/l (normal value) | <0.2 mg/l (normal value) | Value of (1) * | (Normal) |
| <0.2 mg/l (normal value) | 0.2 mg/l < (abnormal value) | Value of (1) * | (Normal) |
| 0.2 mg/l < (abnormal value) | <0.2 mg/l (normal value) | Value of (1) * | (Abnormal) |
| 0.2 mg/l < (abnormal value) | 0.2 mg/l << 10 mg/l (abnormal value) | {value of (1) − value of (2)} ÷ 1000 | (Abnormal) |
| 0.2 mg/l < (abnormal value) | 10 mg/l < (abnormal value) | Reanalysis | None |

In the same way as above, if the measured value of sample (B) is outside the normal range, the analyzer may divide the measured value into several classes so that the result of analysis of sample (A) is interpreted meaningfully. The analyzer may also divide the measured value of sample (A) into more classes and indicates the value of sample (A) which is calculated taking into account an increase due to anticipated carryover from sample (B).

EXAMPLE 3

In this example, it is assumed that an immunological analyzer analyzes β-2-microglobulin (B2M) to test kidney function. It is expected that the urine sample (A) is contaminated with a carryover (1000 ppm) from the serum sample (B). The normal value of B2M is approximately 0.2 mg/l or less for serum and plasma samples and approximately 0.02 mg/l for urine samples. The measured values in the normal range may greatly vary depending on the kind of samples. This is the case for albumin in serum plasma and urine samples and fibrinogen in serum and plasma samples.

According to the present invention, the automated analyzer is programmed such that it carries out tests following the flow chart explained below, and displays or prints the result in the format shown in Tables 5 and 6.

TABLE 5

| Analysis of urine sample (A) for B2M | Analysis of serum sample (B) for B2M | Analysis of sample (A) for B2M | Analysis of sample (A) for B2M |
| --- | --- | --- | --- |
| Measured value (1) | Measured value (2) | Result indicated | Comments indicated |
| <0.02 mg/l | <0.2 mg/l | Value of (1) * | (Normal) |

TABLE 5-continued

| Analysis of urine sample (A) for B2M | Analysis of serum sample (B) for B2M | Analysis of sample (A) for B2M | Analysis of sample (A) for B2M |
| --- | --- | --- | --- |
| (normal value) <0.02 mg/l (normal value) | (normal value) 0.2 mg/l < (abnormal value) | Value of (1) * | (Normal) |
| 0.02 mg/l < (abnormal value) | <0.2 mg/l (normal value) | Reanalysis | none |
| 0.02 mg/l < (abnormal value) | 0.2 mg/l << 10 mg/l (abnormal value) | Reanalysis | none |
| 0.02 mg/l < (abnormal value) | 10 mg/l < (abnormal value) | Reanalysis | none |

TABLE 6

| Analysis of urine sample (A) for B2M | Analysis of serum sample (B) for B2M | Analysis of sample (A) for B2M | Analysis of sample (A) for B2M |
| --- | --- | --- | --- |
| Measured value (1) | Measured value (2) | Result indicated | Comments indicated |
| <0.02 mg/l (normal value) | <0.2 mg/l (normal value) | Value of (1) * | (Normal) |
| <0.02 mg/l (normal value) | 0.2 mg/l < (abnormal value) | Value of (1) * | (Normal) |
| 0.02 mg/l < (abnormal value) | <0.2 mg/l (normal value) | Value of (1) * | (Abnormal) |
| 0.02 mg/l < (abnormal value) | 0.2 mg/l << 10 mg/l (abnormal value) | Reanalysis | none |
| 0.02 mg/l < (abnormal value) | 10 mg/l < (abnormal value) | Reanalysis | none |

(1) The measured value of sample (A) has been found to be 0.01 mg/l which is normal for B2M.

Then, the analyzer indicates that the result of analysis of sample (A) is 0.01 mg/l.

(2) The measured value of sample (A) has been found to be 0.1 mg/l which is outside the normal range for B2M; and the measured value of sample (B) has been found to be 0.1 mg/l which is normal for B2M.

Then, the analyzer indicates that the result of analysis of sample (A) is 0.1 mg/l. Alternatively, the analyzer indicates the value of 0.0999 mg/l which is calculated by subtracting the value of anticipated carryover from the result of analysis of sample (A). In other words, the analyzer indicates with considerably high probability that the result is outside the normal range.

(3) The measured value of sample (A) has been found to be 0.1 mg/l which is outside the normal range for B2M; and the measured value of sample (B) has been found to be 10 mg/l which is outside the normal range for B2M.

Then, the analyzer masks the result of analysis of sample (A) and indicates that it is necessary to take a sample again and to perform analysis again.

(4) The measured value of sample (A) has been found to be 1.0 mg/l which is outside the normal range for B2M; and the measured value of sample (B) has been found to be 10 mg/l which is outside the normal range for B2M.

Then, the analyzer masks the result of analysis of sample (A) and indicates that it is necessary to take a sample again and to perform analysis again. Alternatively, the analyzer indicates the value of 0.99 mg/l or the value of 1.0 mg/l, the former being calculated by subtracting the value of anticipated carryover from the result of analysis of sample (A), and the latter being calculated by not subtracting the value of anticipated carryover from the result of analysis of sample (A). In other words, the analyzer indicates with considerably high probability that the result is outside the normal range.

The analyzer may be set up such that the analyzer analyzes sample (B) after the analyzer has analyzed sample (A) or the analyzer analyzes samples (A) and (B) consecutively.

In the case where the result of analysis and measurement is (3) or (4) mentioned above, its interpretation involves some difficulties. However, in the case where the result of analysis and measurement is (1) or (2) mentioned above, it is not scientifically unreasonable to interpret the result of analysis of sample (A) as being negative or in the normal range.

In the case where the result of analysis and measurement is (3) or (4) mentioned above, it may be desirable to perform sampling and analysis again; however, it may also be possible to predict an approximately correct value of sample (A) if one carefully considers the result of analysis and measurement, the interpretation of the result, and the algorithm.

It is to be understood from the above-mentioned examples of the present invention that in the case where analysis is performed on the sample which has previously been analyzed once or more and which might have been affected by carryover in the previous analysis, it is necessary to incorporate the following method for performing inspection or displaying results into the analyzer to cope with said situation. Thus, it is possible to avoid not performing analysis on the particular sample or nullifying the effectiveness of the measured values.

(1) The measured value of inspection item of a particular sample is negative or in the normal range, then the analyzer regards the measured value as effective and indicates the result.

(2) The measured value of inspection item of a particular sample is positive or in the gray zone, or outside the normal range, then the analyzer performs analysis on the sample which might have caused carryover to the particular sample. If the result of the analysis is negative or in the normal range, the analyzer regards the measured value as effective and indicates the result. The analyzer may add some comment to the result.

The analyzer performs analysis simultaneously on both the particular sample and the sample which might have caused carryover to the particular sample and then interprets the result of analysis of the particular sample based on the result of analysis of the two samples.

(3) Despite the fact that the measured value of analysis of a particular sample is negative or positive, or in the normal range or outside the normal range, the analyzer performs analysis on the sample, which might have caused carryover to the particular sample, for a desired inspection item. In the case where the extent of carryover to the particular sample is roughly predicted from the measured value, then the analyzer may indicate the value calculated by subtracting the predicted extent of carryover from the measured value of the particular sample, with or without comments interpreting the result concluded from the calculated value.

The above-mentioned examples of the present invention permit one to utilize the same sample over and over again. For example, if the ratio of positive in ordinary health examination is about 5%, then it is only necessary to take a sample again from the same patient for 0.05×0.05=1/400, and the remaining 399/400 can be used again.

Therefore, in the case where a sample which has been previously analyzed once or more is analyzed again for an inspection item which is expected to have been affected by carryover from the previously analyzed sample, then it is not necessary to take another sample from the patient. This greatly alleviates the patient's pain and reduces the amount of the doctor's labor and associated cost.

The automated analyzer of the present invention greatly improves the efficiency of inspection work and saves the time and cost necessary for resampling. In addition, the automated analyzer gives an instruction for inspection during a series of inspection operations, so that it rapidly and efficiently tells the doctor and other persons concerned the result of inspection and measurement.

The automated analyzer of the present invention permits one to resume analysis automatically or manually in case of possible failure. Therefore, it permits one to rapidly cope with the failure in analysis.

What is claimed is:

1. A method of biochemical analysis in which a plurality of different samples that are subject to carryover contamination are analyzed successively for an analyte of interest with a same sampling probe to measure quantities of the analyte to provide measured values of the quantities;

comparing the measured values of the analyte to determine if the measured values are within an allowable range, including comparing first and second measured values corresponding to successively analyzed samples, such that when the second one of the measured values is determined to be outside the allowable range, providing a result of analysis of outside the allowable range for said second measured value only if the first measured value corresponding to a previous one of the successively analyzed samples is determined to be within the allowable range.

2. A method of biochemical analysis defined in claim 1, wherein when the first measured value corresponding to the previous one of the successively analyzed samples is determined to be outside the allowable range, a next succeeding one of the successively analyzed samples having the second one of the measured values is subject to reanalysis before providing the result of analysis.

3. A method of biochemical analysis in which a plurality of different samples that are subject to carryover contamination are successively analyzed for an analyte of interest with a same sampling probe to measure quantities of the analyte to provide measured values of the quantities;

comparing the measured values of the analyte to determine if the measured values are within an allowable range, including comparing first and second measured values corresponding to successively analyzed samples, such that when the second one of the measured values is determined to be outside the allowable range, adjusting the second measured value by a predicted amount of a carryover contaminant from a previous one of the successively analyzed samples and then determining whether the second measured value is within an allowable range.

4. An automated analyzer, comprising:

a sampling probe to dispense samples, reaction vessels to mix the dispensed sample and reagent in the vessel, a photometer to measure a reaction of a sample and reagent in the reaction vessel, a microcomputer to perform calculations and displays the results of the measurement, storage means to store the calculated results, wherein, the automated analyzer successively analyzes a plurality of different samples that are subject to carryover contamination for an analyte of interest by comparing the measured values to determine if the measured values are within an allowable range and thus are normal, including comparing first and second measured values corresponding to successively analyzed samples, and when the second one of the measured values is determined to be outside the allowable range, providing a result of analysis of abnormal for the analyzed sample corresponding to said second measured value only if the first measured value corresponding to a previous one of the successively analyzed samples is determined to be within the allowable range; and when the second one of the measured values is determined to be outside the allowable range and the first measured value corresponding to a previous one of the successively analyzed samples is determined to be outside the allowable range, subjecting the analyzed sample corresponding to said second measured value to reanalysis before providing the result of analysis.

5. An automated analyzer defined in claim 4, further comprising:

a storage means to store a predicted amount of carryover contamination, and said analyzer adjusting the second measured value by a predicted amount of the carryover contamination from a previous one of the successively analyzed samples and then determining whether the second measured value is within an allowable range.

* * * * *